US010667943B2

(12) United States Patent
Parunak et al.

(10) Patent No.: US 10,667,943 B2
(45) Date of Patent: Jun. 2, 2020

(54) NOZZLE

(71) Applicant: Ben Z. Cohen, New York, NY (US)

(72) Inventors: Gene Parunak, Saline, MI (US);
Robert C. Martineau, Chippewa Falls, WI (US); Aaron J. Munsinger, Elk Mound, WI (US)

(73) Assignee: Ben Z. Cohen, New York, NY (US)

( * ) Notice: Subject to any disclaimer, the term of this patent is extended or adjusted under 35 U.S.C. 154(b) by 135 days.

(21) Appl. No.: 14/385,224

(22) PCT Filed: Mar. 13, 2013

(86) PCT No.: PCT/US2013/030882
§ 371 (c)(1),
(2) Date: Sep. 15, 2014

(87) PCT Pub. No.: WO2013/138466
PCT Pub. Date: Sep. 19, 2013

(65) Prior Publication Data
US 2015/0038925 A1 Feb. 5, 2015

Related U.S. Application Data

(60) Provisional application No. 61/610,138, filed on Mar. 13, 2012.

(51) Int. Cl.
A61F 9/00 (2006.01)
B05B 1/06 (2006.01)
(Continued)

(52) U.S. Cl.
CPC .............. A61F 9/0008 (2013.01); B05B 1/02 (2013.01); B05B 1/06 (2013.01); B05B 1/28 (2013.01); B05B 1/3402 (2018.08)

(58) Field of Classification Search
CPC ........ A61F 9/0008; A61F 9/0026; B05B 1/06; B05B 1/34; B05B 1/02; B05B 1/28; B05B 1/3402
(Continued)

(56) References Cited

U.S. PATENT DOCUMENTS 4,909,801 A * 3/1990 Casey ............... A61F 9/0026
222/210
5,007,905 A * 4/1991 Bauer ............... A61F 9/0026
604/295

(Continued)

FOREIGN PATENT DOCUMENTS

EP 2332438 A1 * 6/2011 ............. A45D 19/02

OTHER PUBLICATIONS

Ashgriz, N. Handbook of Atomization and Sprays Theory and Applications. Springer, 2011, pp. 628-629. (Year: 2011).*

Primary Examiner — Michael E Barr
Assistant Examiner — Kevin G Lee
(74) Attorney, Agent, or Firm — Budzyn IP Law, LLC

(57) ABSTRACT

A nozzle is provided herein for ophthalmic dispensers which is configured to accommodate microdosing. The nozzle includes a converging pathway. Preferably, the pathway converges so as to impart momentum to liquid passing therethrough through an increase of velocity. A tapered portion may be provided flared openly from the inlet to best accept liquid flow thereinto and provide a funneling effect into the flowpath. Preferably, the flowpath terminates at an outlet which is internally un-radiused and circumscribed by a chamfered surface.

18 Claims, 2 Drawing Sheets

(51) Int. Cl.
*B05B 1/28* (2006.01)
*B05B 1/34* (2006.01)
*B05B 1/02* (2006.01)

(58) Field of Classification Search
USPC .............................. 222/420, 210, 570, 460
See application file for complete search history.

(56) References Cited

U.S. PATENT DOCUMENTS

| | | | | |
|---|---|---|---|---|
| 5,152,435 | A * | 10/1992 | Stand | A61F 9/0008 |
| | | | | 222/309 |
| 7,651,011 | B2 * | 1/2010 | Cohen | B05B 11/0059 |
| | | | | 222/321.2 |
| 8,684,980 | B2 * | 4/2014 | Hunter | A61B 5/0059 |
| | | | | 604/298 |
| 2002/0084290 | A1 * | 7/2002 | Materna | B01L 3/0241 |
| | | | | 222/420 |
| 2003/0197074 | A1 * | 10/2003 | McNerney | B05B 1/3421 |
| | | | | 239/541 |
| 2004/0050881 | A1 * | 3/2004 | Deussen | B65D 47/18 |
| | | | | 222/420 |
| 2006/0069358 | A1 * | 3/2006 | Gerondale | A61F 9/0008 |
| | | | | 604/298 |
| 2009/0152281 | A1 * | 6/2009 | Bowes | A45D 19/02 |
| | | | | 220/694 |
| 2010/0211027 | A1 * | 8/2010 | Pine | A61F 9/0008 |
| | | | | 604/290 |
| 2013/0153677 | A1 * | 6/2013 | Leen | B01L 3/0268 |
| | | | | 239/102.1 |

\* cited by examiner

NOZZLE

CROSS-REFERENCES TO RELATED APPLICATIONS

This application is a National Stage Application under 35 U.S.C. § 371 of PCT International Application No. PCT/US2013/030882, filed Mar. 13, 2013, which claims priority to U.S. Provisional Patent Application No. 61/610,138, filed on Mar. 13, 2012, the entire contents of which are incorporated by reference herein.

BACKGROUND OF THE INVENTION

This invention relates to nozzles for ophthalmic dispensers.

Various dispensers for delivering medicament, and other active ingredients, to the eye are known in the prior art. Eye droppers and dropper bottles are used extensively to deliver liquid doses to the eyes of patients. Typical droppers and dropper bottles can only produce dose volumes of certain sizes, with no ability to provide smaller doses. As such, it is well recognized that a large percentage of administered ophthalmic liquid that is administered topically is lost by drainage, either externally or through nasolacrimal drainage.

Dispensers have been developed in the prior art which can generate dose sizes in much smaller volumes than those provided by typical droppers and dropper bottles, such doses being in the range of 5-15 microliters. Dispensers for delivering such doses are known in the prior art, such as U.S. Pat. No. 5,152,435, which issued Oct. 6, 1992; U.S. Pat. No. 5,881,956, which issued Mar. 16, 1999; U.S. Pat. No. 6,513,682, which issued Feb. 4, 2003; U.S. Pat. No. 6,854,622, which issued Feb. 15, 2005; U.S. Pat. No. 6,991,137, which issued on Jan. 31, 2006; U.S. Pat. No. 7,014,068, which issued on Mar. 21, 2006; U.S. Pat. No. 7,073,733, which issued on Jul. 11, 2006; U.S. Pat. No. 7,131,559, which issued on Nov. 7, 2006; U.S. Pat. No. 7,207,468, which issued on Apr. 24, 2007; U.S. Pat. No. 7,261,224, which issued on Aug. 28, 2007; and U.S. Pat. No. 7,651,011, which issued on Jan. 26, 2010. These references are all incorporated by reference herein.

The aforesaid dispensers may achieve microdosing with doses in the range of 5-15 microliters. With such microdosing, concerns exist over repeatability within a target range. With such small doses, slight variability impacts the dose size.

SUMMARY OF THE INVENTION

A nozzle is provided herein for ophthalmic dispensers which is configured to accommodate microdosing. The nozzle includes a converging pathway. Preferably, the pathway converges so as to impart momentum to liquid passing therethrough through an increase of velocity. A tapered portion may be provided flared openly from the inlet to best accept liquid flow thereinto and provide a funneling effect into the flowpath. Preferably, the flowpath terminates at an outlet which is internally un-radiused and circumscribed by a chamfered surface.

To further enhance the ability of the nozzle to administer repeated uniform doses, one or more of the liquid-contacting surfaces may be treated to be hydrophobic. Additionally, surfaces surrounding liquid-contacting surfaces may be also treated to be hydrophobic.

Advantageously, with the subject invention, a nozzle is provided which can direct a dose for administration, with minimal attraction to the nozzle.

These and other features of the invention will be better understood through a study of the following detailed description and accompanying drawings.

DETAILED DESCRIPTION OF THE INVENTION

Figure 1:
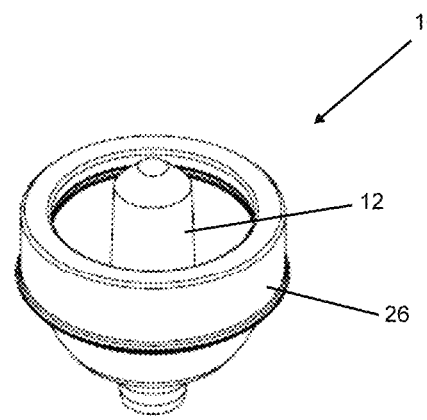
FIG. 1 is a front perspective view of a nozzle formed in accordance with the subject invention.
Figure 2:
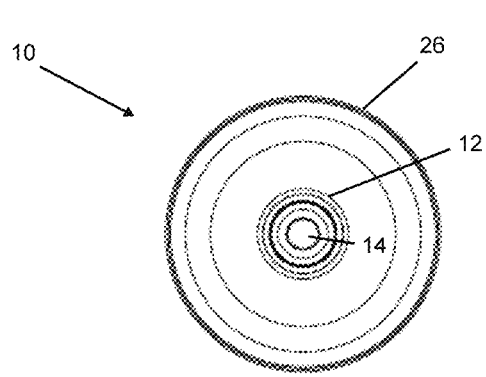
FIG. 2 is a rear elevational view of a nozzle formed in accordance with the subject invention.
Figure 3:
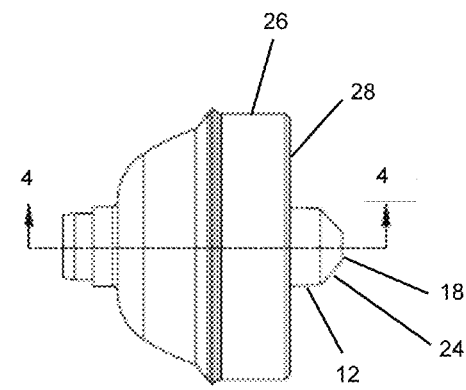
FIG. 3 is a side elevational view of a nozzle formed in accordance with the subject invention.
Figure 4:
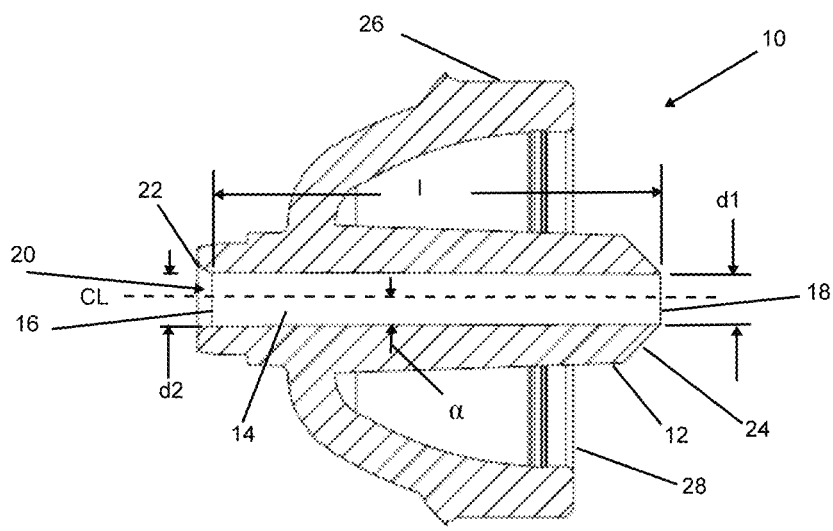
FIG. 4 is a cross-sectional view taken along line 4-4 of FIG. 3.

With reference to the Figures, a nozzle 10 is provided. The nozzle 10 is particularly well-suited for administering microdoses, e.g., ophthalmic doses in the range of 5-15, even 5-20, microliters.

As shown in the Figures, the nozzle 10 is preferably a unitary piece manufactured separately from other components, such as pump components. Preferably, the nozzle 10 is formed from thermoplastic material and is preferably formed by molding. By being separately formed, the tolerances of the nozzle 10 may be tightly controlled. Although less preferred, the nozzle 10 may be formed integrally with other components of a pump.

The nozzle 10 includes an elongated, tubular nozzle portion 12 which defines a liquid pathway 14 therethrough. The liquid pathway 14 extends between an inlet 16 and an outlet 18 so that liquid introduced through the inlet 16 may pass to the outlet 18 through the liquid pathway 14.

The liquid pathway 14 is preferably elongated having a length l which is more than eight times greater than diameter d1 of the outlet 18. The length l may be more than ten times greater than diameter d1 of the outlet 18. Preferably, the liquid pathway 14 is formed to be convergent from the inlet 16 to the outlet 18. With this arrangement, liquid passing through the liquid pathway 14 experiences a momentum buildup through an increase of velocity while travelling from the inlet 16 to the outlet 18. The momentum buildup allows for a dose to be delivered at a higher velocity. This allows for the dose to be delivered in a more compact, less broken-up manner. Ideally, a dose of a singe drop is delivered. If sufficient momentum is not imparted, microbubbles form in the liquid with the dose possibly breaking up to some extent.

Preferably, the convergence is only slight so that the flow characteristics of the liquid passing through the liquid pathway 14 are only slightly altered. In addition, fluid turbulence is minimized. It is preferred that the convergence be at a constant rate from the inlet 16 to the outlet 18. Preferably, the angle of convergence α is in the range of 0.25-1.0 degrees relative to the longitudinal axis CL of the liquid pathway 14. With the convergent arrangement of the liquid pathway 14, the inlet 16 is provided with a larger diameter than the outlet 18. Preferably, the ratio of the diameter d2 of the inlet 16 to the diameter d1 of the outlet 18 is in the range of 1.05-1.6, more preferably 1.05-1.5, more preferably 1.05-1.4, more preferably 1.05-1.3, more preferably 1.05-1.2, more preferably 1.05-1.1, and most preferably 1.08.

Preferably, a tapered portion 20 extends, and diverges away, from the inlet 16. This provides an enlarged opening to receive liquid which is then funneled through the tapered portion 20 into the liquid pathway 14. The tapered portion 20 includes an inner edge 22 which preferably extends continuously from the inlet 16. The inner edge 22 is defined with the taper of the tapered portion 20. The taper may be provided with the inner edge 22 being arcuate, chamfered and combinations thereof. Surface interruptions such as straight wall portions or ledges may be provided on the inner edge 22, particularly if such enhances manufacturability. With the tapered portion 20, an overall decrease in diameter towards the inlet 16 is provided, such decrease in diameter being continuous or discontinuous.

The tapered portion 20 also desirably may reduce vorticity imparted to the liquid as being delivered through the nozzle 10. Changes in direction in flow may cause liquid to have vorticity, which can also lead to dose break-up. A laminar flow is ideally sought. With typical pump arrangements, liquid is caused to significantly change direction (e.g., a 90° change in direction) in being fed from a fluid path and into a nozzle. A significant change in direction may impart vorticity. The tapered portion 20 may ameliorate this effect by allowing the liquid to traverse a tapered inlet into the nozzle 10 with a more gradual change of direction being applied than if no tapered portion 20 was provided. This is more advantageous where an inlet fluid path is positioned at a generally right angle relative to the nozzle 10.

It is also preferred that the nozzle portion 12 be formed with the outlet 18 being internally un-radiused (the outlet 18 lying wholly in a plane perpendicular to the longitudinal axis CL) and with a reduced diameter section 24 about the outlet 18. As shown in the Figures, the reduced diameter section 24 preferably is a chamfered section which extends from the outlet 18 and flares inwardly therefrom so as to minimize portions of the nozzle portion 12 being within a plane coinciding with the outlet 18 (the plane being perpendicular to the longitudinal axis CL). With this arrangement, a liquid dose discharged from the outlet 18 will have minimal surface contact with the nozzle portion 12 about the outlet 18.

To further enhance the ability of the nozzle 10 to administer repeated uniform doses of liquid, the liquid pathway 14 is preferably treated to be hydrophobic. Various techniques may be utilized for hydrophobic treatment, including plasma treatment. In this manner, capillary, or other attraction, may be minimized between the nozzle 10 and the dose. Such attractive force may disrupt the dose during delivery. Portions surrounding the liquid pathway 14, such as the tapered portion 20 and the reduced diameter section 24, may be also hydrophobically treated. It may be most practical to treat the entire nozzle 10 hydrophobically.

To permit mounting of the nozzle portion 12, a mounting ring 26 may extend from the nozzle portion 12. Preferably, the mounting ring 26 is bowl-shaped. The mounting ring 26 circumscribes the nozzle portion 12 such that the outlet end of the nozzle portion 12 is on the inner side of the bowl of the mounting ring 26. Preferably, a portion of the nozzle portion 12 extends rearwardly from the mounting ring 26 so that the inlet 16 is spaced from the mounting ring 26. It is also preferred that the outlet 18 extend beyond the mounting ring 26 so as to be located exteriorly thereof (e.g., the outlet 18 is located beyond rim 28 of the mounting ring 26).

Figure 5:
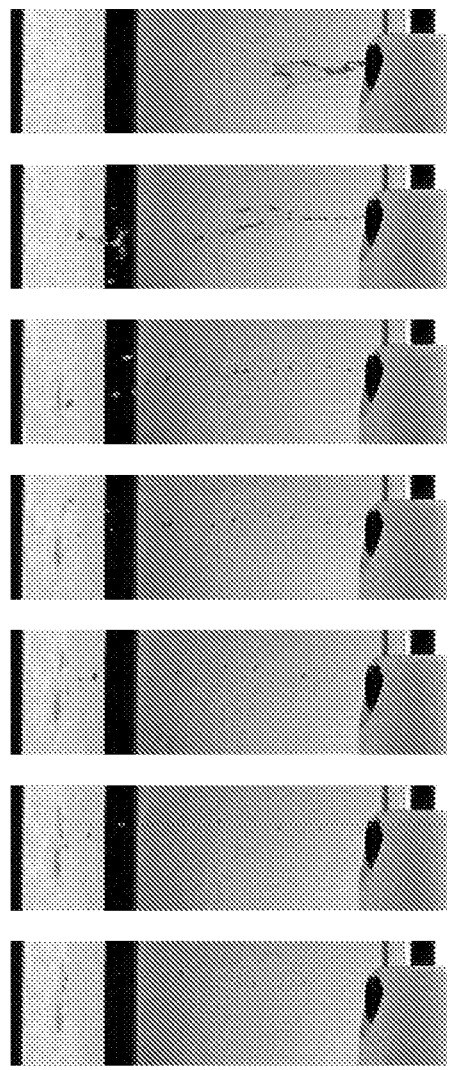
FIG. 5 is a series of stop-motion photographs showing delivery of a dose by a prior art nozzle.

FIG. 5 includes a series of photographs showing with stop-motion photography, the delivery of a 6.5 µL dose of water purified by reverse osmosis with methylene blue dye using a prior art nozzle with a pump. The nozzle includes a 0.179 inch liquid pathway which diverges to an outlet having a diameter of 0.0502 inches with an internal tip radius of 0.005 inches.

Figure 6:
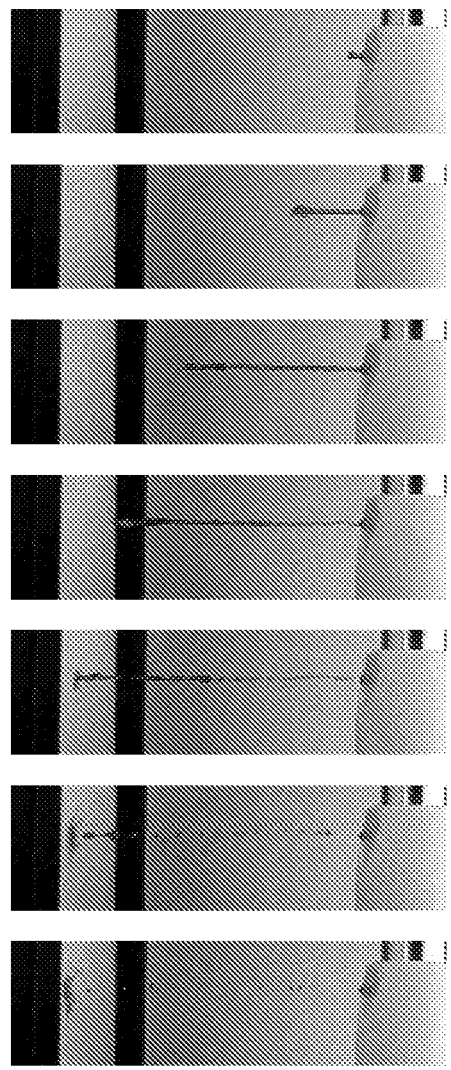
FIG. 6 is a series of stop-motion photographs showing delivery of a dose by a nozzle formed in accordance with the subject invention.

FIG. 6 includes a series of photographs showing with stop-motion photography, the delivery of a 19.8 µL dose of water purified by reverse osmosis with methylene blue dye using a nozzle formed in accordance with the subject invention and using the same type of pump as discussed with respect to FIG. 5. The nozzle here includes a 0.315 inch liquid pathway converging from a inlet of 0.039 inches to an outlet of 0.036 inches with the outlet having no internal tip radius. In addition, the liquid pathway is hydrophobically treated.

As can be seen, the dose delivered with the nozzle in FIG. 6 is more directed than with the prior art nozzle of FIG. 5. It is noted that the dose in FIG. 6 has some break-up into smaller drops. However, overall dose is delivered more intact as a single unit with the nozzle of FIG. 6 as compared with the dose of FIG. 5. This aides in delivering a maximum amount of a dose. Further to the extent a dose breaks up, the smaller drops maintain better linearity in being delivered by the nozzle of FIG. 6 as compared with the delivery of the dose of FIG. 5. This results in a greater amount of dose reaching a target site.

What is claimed is:

1. An ophthalmic liquid dispenser for delivering a pumped dose comprising a nozzle, the nozzle comprising:
    a nozzle portion defining a liquid pathway extending between an inlet and an outlet for discharging the pumped dose, said liquid pathway converging from said inlet to said outlet, wherein a length is defined between said inlet and said outlet, said length being more than eight times greater than the diameter of said outlet, and wherein a longitudinal axis extends along said liquid pathway, said liquid pathway converging along the length at an angle of convergence in the range of 0.25-1.0 degrees relative to said longitudinal axis, wherein said liquid pathway is treated to be hydrophobic, wherein the ratio of the diameter of said inlet to the diameter of said outlet is in the range of 1.05-1.6; and,
    a mounting ring extending from a mid-position on said nozzle portion with first and second portions of said nozzle portion extending axially in opposing directions from said mid-position, said inlet being located on said first portion and said outlet being located on said second portion.

2. An ophthalmic liquid dispenser as in claim 1, wherein the ratio of the diameter of said inlet to the diameter of said outlet is in the range of 1.05-1.5.

3. An ophthalmic liquid dispenser as in claim 2, wherein the ratio of the diameter of said inlet to the diameter of said outlet is in the range of 1.05-1.4.

4. An ophthalmic liquid dispenser as in claim 3, wherein the ratio of the diameter of said inlet to the diameter of said outlet is in the range of 1.05-1.3.

5. An ophthalmic liquid dispenser as in claim 4, wherein the ratio of the diameter of said inlet to the diameter of said outlet is in the range of 1.05-1.2.

6. An ophthalmic liquid dispenser as in claim 5, wherein the ratio of the diameter of said inlet to the diameter of said outlet is in the range of 1.05-1.1.

7. An ophthalmic liquid dispenser as in claim 1, further comprising a tapered portion extending, and diverging away, from said inlet.

8. An ophthalmic liquid dispenser as in claim 7, wherein said tapered portion includes an inner edge which extends continuously from said inlet.

9. An ophthalmic liquid dispenser as in claim 8, wherein said tapered edge is provided with the shape selected from the group consisting of arcuate, chamfered, and combinations thereof.

10. An ophthalmic liquid dispenser as in claim 1, wherein said second portion having an exterior surface defining a reduced diameter section about said outlet.

11. An ophthalmic liquid dispenser as in claim 10, wherein said reduced diameter section includes a chamfered section which extends from said outlet and flares inwardly therefrom.

12. An ophthalmic liquid dispenser as in claim 1, wherein said mounting ring circumscribes said nozzle portion.

13. An ophthalmic liquid dispenser as in claim 1, wherein said mounting ring is generally bowl-shaped.

14. An ophthalmic liquid dispenser as in claim 13, wherein said outlet is located on an inner side of the bowl shape of said mounting ring.

15. An ophthalmic liquid dispenser as in claim 14, wherein said outlet extends beyond said mounting ring.

16. An ophthalmic liquid dispenser as in claim 1, wherein the nozzle is unitary.

17. An ophthalmic liquid dispenser as in claim 1, wherein the nozzle is formed of thermoplastic material.

18. An ophthalmic liquid dispenser as in claim 1, wherein said outlet is internally un-radiused.

* * * * *